(12) United States Patent
Toraya et al.

(10) Patent No.: US 9,417,195 B2
(45) Date of Patent: Aug. 16, 2016

(54) METHOD AND ITS APPARATUS FOR X-RAY DIFFRACTION

(75) Inventors: Hideo Toraya, Tachikawa (JP); Shigeru Munekawa, Tokyo (JP)

(73) Assignee: RIGAKU CORPORATION, Tokyo (JP)

( * ) Notice: Subject to any disclaimer, the term of this patent is extended or adjusted under 35 U.S.C. 154(b) by 100 days.

(21) Appl. No.: 13/812,567

(22) PCT Filed: Jul. 29, 2011

(86) PCT No.: PCT/JP2011/067551
§ 371 (c)(1),
(2), (4) Date: Jan. 28, 2013

(87) PCT Pub. No.: WO2012/015053
PCT Pub. Date: Feb. 2, 2012

(65) Prior Publication Data
US 2013/0129052 A1 May 23, 2013

(30) Foreign Application Priority Data
Jul. 30, 2010 (JP) ................................ 2010-172582

(51) Int. Cl.
*G01N 23/207* (2006.01)
*G01N 23/20* (2006.01)
*G01N 23/205* (2006.01)

(52) U.S. Cl.
CPC ........ *G01N 23/20008* (2013.01); *G01N 23/207* (2013.01); *G01N 23/2055* (2013.01); *G01N 2223/0566* (2013.01)

(58) Field of Classification Search
CPC ... G01N 23/20; G01N 23/207; G01N 23/223; G01N 23/20008; G01N 23/20016; G01N 23/20075; G01N 2223/076; G01N 23/205; G01N 23/2055; G01N 2223/0566; G21K 1/02; G21K 1/04; G21K 1/06; G21K 1/065
USPC ........ 378/70, 71, 73, 81, 84, 90, 92, 98, 98.8, 378/143, 147, 160, 75
See application file for complete search history.

(56) References Cited

U.S. PATENT DOCUMENTS

| | | | |
|---|---|---|---|
| 5,600,303 A * | 2/1997 | Husseiny et al. | 340/568.1 |
| 6,798,863 B2 | 9/2004 | Sato | |
| 2007/0111881 A1* | 5/2007 | Harel et al. | 502/60 |
| 2009/0210366 A1* | 8/2009 | Sakata et al. | 706/13 |
| 2009/0274274 A1 | 11/2009 | He et al. | |

FOREIGN PATENT DOCUMENTS

| | | |
|---|---|---|
| JP | 55-158544 | 12/1980 |
| JP | 2-266249 | 10/1990 |
| JP | 5-126765 | 5/1993 |

(Continued)

*Primary Examiner* — Glen Kao
(74) *Attorney, Agent, or Firm* — Mattingly & Malur, PC (57) ABSTRACT

In order to realize a compact and lightweight X-ray diffraction apparatus not requiring a goniometer, an apparatus for X-ray diffraction includes a first X-ray irradiating unit and a second X-ray irradiating unit that irradiate shaped X-rays on a same region of the surface of the sample from respective directions; an X-ray detecting unit that detects a first diffracted X-ray emanated from the region of the sample where the X-ray is irradiated by the first X-ray irradiating unit and a second diffracted X-ray emanated from the region of the sample where the X-ray is irradiated from the second X-ray irradiating unit; and an X-ray diffraction signal processing unit that processes a signal acquired by detecting the first diffracted X-ray and the second diffracted X-ray emanated from the same region of the sample with the X-ray detecting unit.

18 Claims, 7 Drawing Sheets

(56) References Cited

FOREIGN PATENT DOCUMENTS

| JP | 5-223994 | 9/1993 |
| JP | 11-6806 | 1/1999 |
| JP | 2002-39970 | 2/2002 |
| JP | 2002-350373 | 12/2002 |

\* cited by examiner

METHOD AND ITS APPARATUS FOR X-RAY DIFFRACTION

TECHNICAL FIELD

The present invention relates to a method for X-ray diffraction in which a characteristic X-ray emitted from an X-ray tube is irradiated to a sample to make an analysis of a material, a portable method for X-ray diffraction using the same, and its apparatus.

BACKGROUND ART

A use of a method for X-ray diffraction has been established as a method of identifying an unknown crystal sample, or as a measurement method of measuring a part of a large sample or a sample mounted on various substrates. With this, there has been an increased demand for a measuring apparatus that can allow an analyzing apparatus, which has conventionally been used in a building, to be used outdoors. Thanks to the recent development in electronic techniques, a power source and a control circuit can be made compact, and lightweight, and can be formed to have reduced power consumption. However, a general method for X-ray diffraction entails a problem that, when a position of a sample is shifted from a predetermined position, a measurement precision or sensitivity is deteriorated. In order to avoid this situation, a mechanical angle measuring device called goniometer described in Patent Literature 1, for example, is used to carry out a measurement of an X-ray diffraction in which a sample is located at a predetermined position.

Patent Literature 2 describes a configuration of using a position-sensitive X-ray detector or accumulative fluorescent material, wherein a diffracted X-ray from a sample is detected with the detector being fixed.

Patent Literature 3 describes a configuration in which a direction of a CCD having position resolution within a linear range is changed between a tangential direction and a radius direction of a Debye ring of a diffracted X-ray so as to detect an intensity of the X-ray.

On the other hand, Patent Literature 4 describes a portable X-ray diffraction apparatus that aims an X-ray diffraction of a specific portion.

CITATION LIST

Patent Literature

| | |
|---|---|
| Patent Literature 1 | JP-A No. 5-223994 |
| Patent Literature 2 | JP-A No. 5-126765 |
| Patent Literature 3 | JP-A No. 11-6806 |
| Patent Literature 4 | U.S. Patent Application Publication No. 2009/0274274 |

SUMMARY OF INVENTION

Technical Problem

In the measurement of the X-ray diffraction, a diffraction intensity of an X-ray to a diffraction angle of the X-ray is measured by an X-ray detector. Therefore, as described in Patent Literature 1, it has to be measured by changing the angle of the sample or the position of the detector for each angle. Accordingly, a mechanical angle measuring device inevitably needs weight in order to attain precision in holding an X-ray source or detector or in changing the angle, which means it is difficult to make the angle measuring device compact and lightweight.

In the X-ray diffraction apparatus described in Patent Literature 2, a position-sensitive X-ray detector is arranged over a wide detection-angle range. However, an incident angle (irradiation angle) of the X-ray to the sample is fixed, so that it is unsuitable for the detection of an X-ray diffraction pattern of a sample in which a direction of a crystal is optional.

The X-ray diffraction apparatus described in Patent Literature 3 has two types of detectors for detecting the tangential direction and radius direction of the Debye ring, wherein these detectors are switched for the detection. Therefore, it is unsuitable for making the apparatus compact.

Patent Literature 4 describes a hand-held X-ray diffraction apparatus. In this apparatus, two detectors are arranged at positions apart from each other, so that the Debye ring in a continuous region cannot be detected, which entails a problem that some information of the diffracted X-ray might be missing.

The present invention is accomplished in order to realize a compact and lightweight apparatus for X-ray diffraction as described above. Specifically, when an X-ray diffraction measurement is carried out, the measurement has conventionally been made under the condition in which a positional relationship among an incident X-ray, a sample, and a diffracted X-ray is surely retained. For example, a diffracted X-ray from a sample is measured by using a characteristic X-ray (when a target is Cu, a wavelength of $K\alpha 1$ is 0.154056 nm) emitted from an X-ray tube. This measurement condition is based upon Bragg law, wherein a mechanical angle setting device called goniometer has been used in order to accurately keep the positional relationship among the X-ray tube, the sample, and the X-ray detector. The mechanical goniometer has large weight, so that it is unsuitable as a device that can be held and used with human power. Further, since it is held by human power, the measurement is not affected by a shift in the position of the sample. Therefore, a method for X-ray diffraction, which is executed without using the goniometer, and an X-ray diffraction apparatus using this method have been desired.

The present invention is accomplished in view of the above-mentioned conventional problems, and aims to provide a method for X-ray diffraction that does not need a goniometer, which is used to adjust a position of a detector, and a compact and lightweight apparatus for this method.

Solution to Problem

In order to attain the foregoing object, the present invention provides an X-ray diffraction apparatus, the apparatus including: plural X-ray irradiating units that irradiate shaped X-rays onto a same surface of a sample from different directions; an X-ray detecting unit that detects plural diffracted X-rays emanated from the sample through the irradiation of the X-rays in the same surface region of the sample by the plural X-ray irradiating units; and an X-ray diffraction signal processing unit that processes signals acquired by detecting the plural diffracted X-rays emanated from the same surface region of the sample by the X-ray detecting unit.

In order to attain the foregoing object, the present invention also provides an X-ray diffraction method including: irradiating X-rays, which are shaped, from plural X-ray irradiating units onto a same surface of a sample from different directions; detecting, by an X-ray detecting unit, plural diffracted X-rays emanated from the sample through the irradiation of the X-rays in the same surface region of the sample by the plural X-ray irradiating units; and processing signals acquired by detecting the plural diffracted X-rays emanated from the same surface region of the sample by the X-ray detecting unit.

Advantageous Effects of Invention

According to the present invention, the X-ray diffraction pattern can be detected in a continuous wide region, whereby a higher detection precision can be attained.

The present invention does not need a goniometer conventionally used for adjusting a position of a detector, and does not have a movable mechanism other than a shutter. Therefore, the present invention can provide a compact and lightweight apparatus.

These and other objects, features and advantages of the invention will be apparent from the following more particular description of preferred embodiments of the invention, as illustrated in the accompanying drawings.

BRIEF DESCRIPTION OF DRAWINGS

FIG. 3A is a side view of an X-ray detector illustrating a relationship between a Debye ring of a diffracted X-ray emanated when an X-ray is irradiated toward the sample from a first X-ray irradiating unit with an angle $\phi 1$, and the X-ray detector, while

FIG. 4A is a side view of an X-ray detector illustrating a relationship between a Debye ring of a diffracted X-ray emanated when an X-ray is irradiated toward the sample from a second X-ray irradiating unit with an angle $\phi 2$, and the X-ray detector, while

DESCRIPTION OF EMBODIMENTS

In the present invention, a position of a diffracted X-ray is detected without using a goniometer, whereby an apparatus is made compact and lightweight, which enhances portability.

Embodiments of the present invention will be described below with reference to the drawings.

First Embodiment

Figure 1:
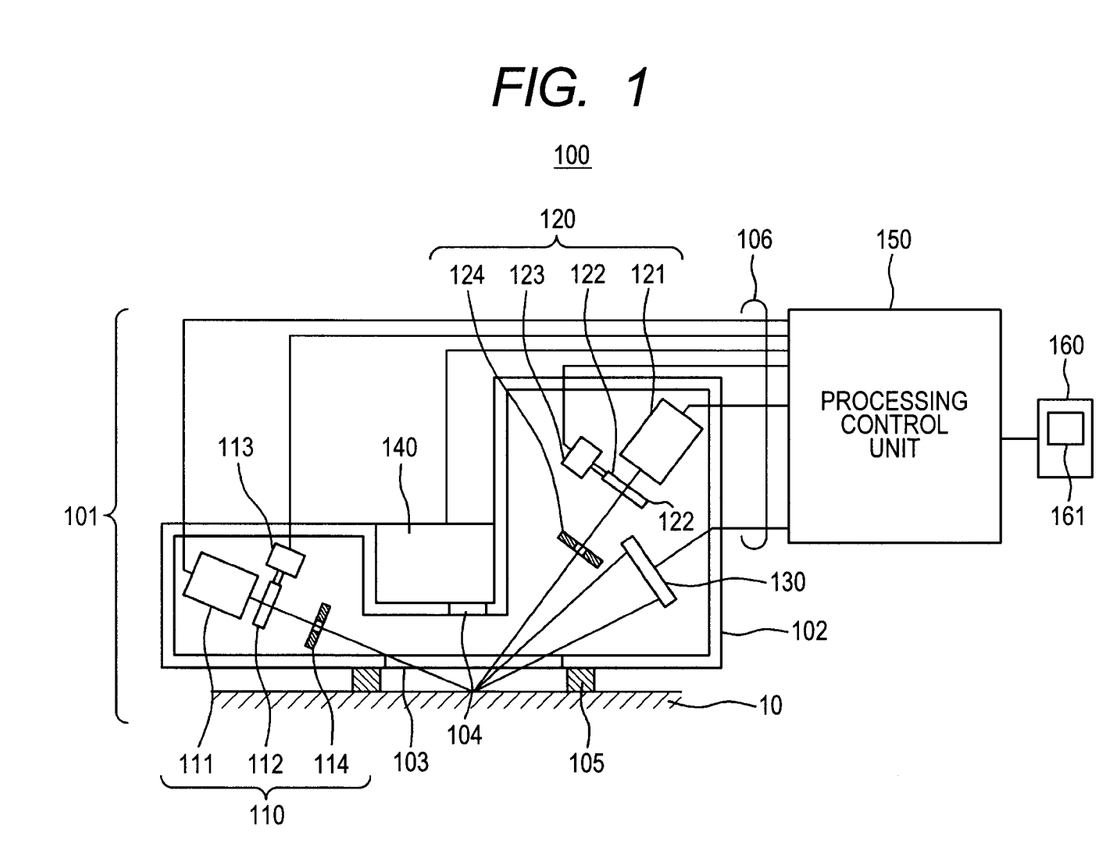
FIG. 1 is a block diagram illustrating an overall structure of an X-ray diffraction apparatus according to a first embodiment and a second embodiment of the present invention.

FIG. 1 illustrates a configuration of a first embodiment.

An X-ray diffraction apparatus 100 according to the first embodiment includes an X-ray diffraction apparatus body 101 having a first X-ray irradiating unit 110, a second X-ray irradiating unit 120, an X-ray detector 130, and a monitor camera 140; a processing control unit 150; and an output unit 160. The first X-ray irradiating unit 110, the second X-ray irradiating unit 120, and the X-ray detector 130 are arranged on the same plane illustrated in FIG. 1.

The first X-ray irradiating unit 110 of the X-ray diffraction apparatus body 101 includes a first X-ray source 111, a first shutter 112, a first actuator 113 that drives the first shutter 112 to open or close the shutter 112, and a first slit device 114 that narrows down the X-ray emitted from the first X-ray source 111.

The second X-ray irradiating unit 120 of the X-ray diffraction apparatus body 101 includes a second X-ray source 121, a second shutter 122, a second actuator 123 that drives the second shutter 122 to open or close the shutter 122, and a second slit device 124 that narrows down the X-ray emitted from the second X-ray source 121.

The X-ray detector 130 is made of a two-dimensional sensor array having sensor devices, which detect the X-ray, arranged two-dimensionally.

The slit device is one of X-ray forming units, and it can be replaced with an X-ray optical device such as a capillary tube, zone plate, or a collimator. Specifically, the first slit device is a first X-ray forming unit, and the second slit device is a second X-ray forming unit. The same is applied to later-described embodiments 2 and 3.

The first X-ray irradiating unit 110, the second X-ray irradiating unit 120, and the X-ray detector 130 are arranged and fixed in a container 102.

The container 102 is formed with an X-ray transmissive window 103 for irradiating the X-rays emitted from the first X-ray irradiating unit 110 and the second X-ray irradiating unit 120 arranged therein to a sample 10 placed at the outside of the container 102. The X-ray transmissive window 103 may be a mere opening or may be partitioned with an X-ray transmissive film. When the X-ray transmissive window 103 is partitioned with the X-ray transmissive film, the container 102 can be evacuated or filled with an inert gas with an unillustrated unit.

In order to be capable of confirming, by the monitor camera 140, the position of the sample 10 where the X-ray is irradiated, a glass window 104 for the monitor is provided at the side where the monitor camera 140 is mounted. An X-ray shield ring 105 for a protection of an X-ray leakage is provided at the outside of the X-ray transmissive window 103 in order to prevent the X-ray from leaking to the outside of the container 102, when the X-ray emitted from the first X-ray irradiating unit 110 or the second X-ray irradiating unit 120 is irradiated to the sample 10.

Figure 2:
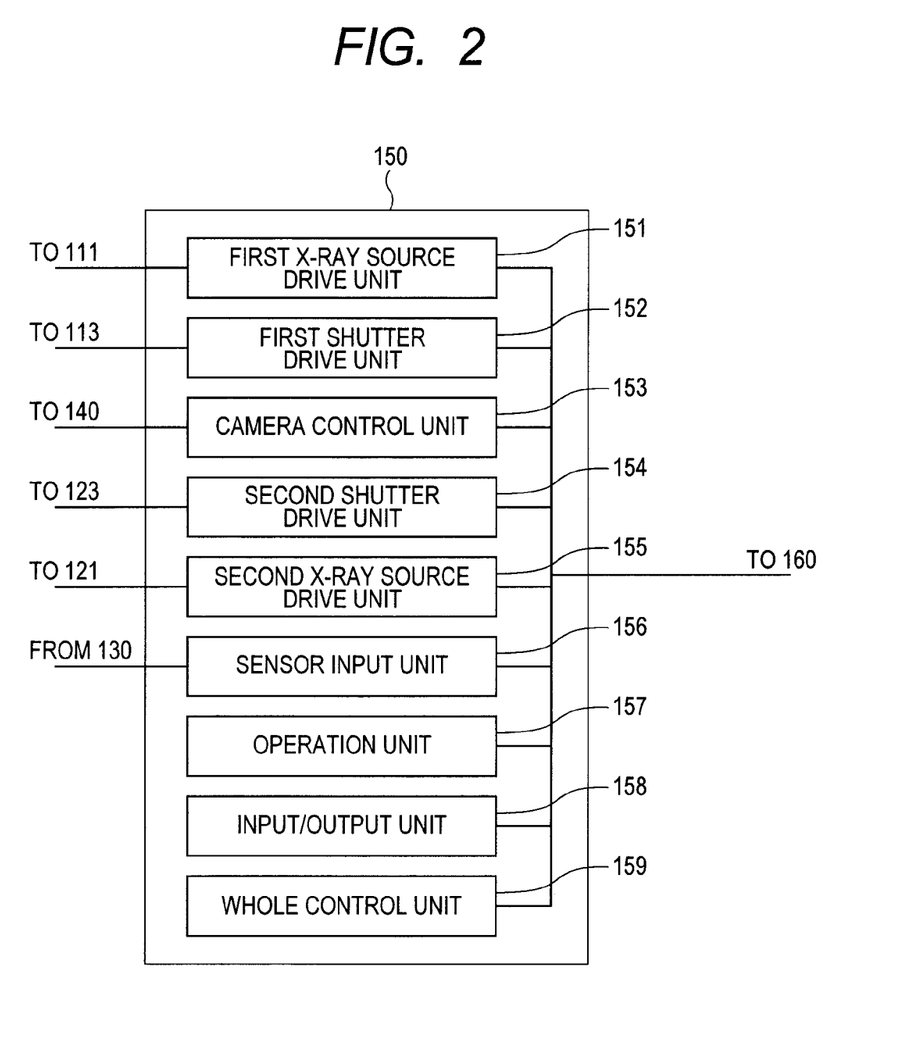
FIG. 2 is a block diagram illustrating a processing control unit of the X-ray diffraction apparatus according to the first embodiment and the second embodiment of the present invention.

As illustrated in FIG. 2, the processing control unit 150 includes a first X-ray source drive unit 151 for driving the first X-ray source 111, a first shutter drive unit 152 for driving the first actuator 113 so as to open and close the first shutter 112, a camera control unit 153 for controlling the monitor camera 140, a second shutter drive unit 154 for driving the second actuator 123 so as to open and close the second shutter 122, a second X-ray source drive unit 155 for driving the second X-ray source 121, a sensor input unit 156 for receiving an output from the X-ray detector 130, an operation unit 157 for calculating an X-ray diffraction angle of the sample 10 by using the output from the X-ray detector 130 received by the sensor input unit 156, an input/output unit 158 that inputs information involved with the irradiation condition of the X-ray and the sample 10 and outputs information involved with the X-ray diffraction angle of the sample 10 obtained from the operation unit 157, and an entire control unit 159 that controls the entire apparatus. The respective units of the processing control unit 150 and the X-ray diffraction apparatus body 101 are separated, wherein they are connected with a cable 106.

The output unit 160 includes a display screen 161, and displays the information involved with the X-ray diffraction angle of the sample 10 outputted from the input/output unit 158 of the processing control unit 150 onto the display screen 161.

A method of measuring the diffraction of the X-ray of the sample 10 with the configuration described above will be described with reference to FIGS. 3 to 5.

Figure 3A:
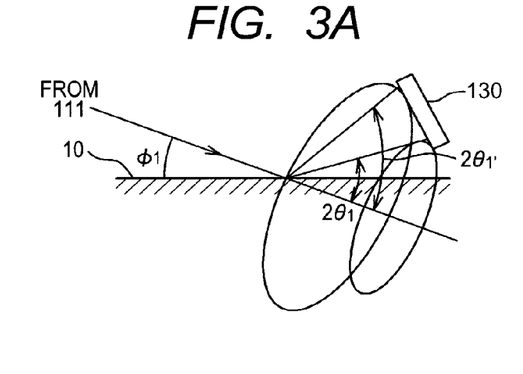

As illustrated in FIG. 3A, when the X-ray having a wavelength of λ from the first X-ray source 111 is transmitted through the first slit device 114 to be shaped, and then, is incident on the sample 10, which is a polycrystalline body, with an incident angle φ1, the diffracted X-ray is emanated according to the orientation of the crystal of the sample 10. When the diffraction angle of the diffracted X-ray with respect to the advancing direction of the incident X-ray is defined as $2\theta_1$, the diffracted X-ray appears on an annular outline (Debye ring) obtained by cutting a cone, in which the incident direction of the X-ray is defined as a central axis and a half of an apex angle is defined as $2\theta_1$ with the position of the sample 10 where the X-ray is irradiated being defined as an apex, along a plane vertical to the central axis.

The diffraction angle $2\theta_1$ is represented as an angle double the incident angle $\theta_1$ of the X-ray to the crystal plane of the sample 10. Specifically, when the position where the diffracted X-ray is emanated is found through the detection of the diffracted X-ray from the sample 10 with the use of the X-ray detector 130, information relating to a crystal lattice length of the sample 10 can be obtained from the incident angle of the X-ray to the sample 10 and the relating to the position where the diffracted X-ray is emanated. When the crystal plane of the sample 10 has random orientations, information relating to the respective crystal planes can be obtained, whereby the inside of the sample 10 can be observed without destroying the sample 10.

Figure 3B:
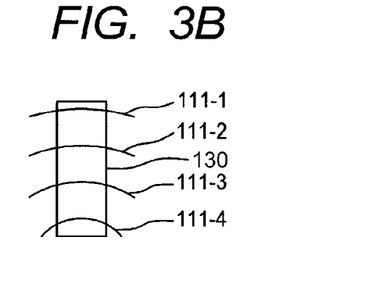
FIG. 3B is front view of the X-ray detector.

FIG. 3B illustrates one example of a state in which the diffracted X-ray from the sample 10 is detected by the X-ray detector 130. Diffracted X-ray patterns 111-1 to 111-4 according to the indexing of the crystal planes of the sample 10 are detected on the detection surface of the X-ray detector 130.

The diffraction angle $2\theta_1$, $\theta_1$ of the diffracted X-ray and the crystal lattice length can be obtained from the positional relationship among the positional information of the convex diffracted X-ray patterns 111-1 to 111-4 on the X-ray detector 130 detected by the X-ray detector 130, the position of the sample 10 where the X-ray is irradiated and the X-ray detector, and the information relating to the X-ray irradiation direction.

It has been described that the X-ray detector 130 is a two-dimensional detector. However, the X-ray detector 30 may be replaced with a linear sensor having devices arranged in a longitudinal direction as illustrated in FIG. 3A, because the position of the Debye ring of the diffracted X-ray projected on the X-ray detector 130 is only found.

Figure 4A:
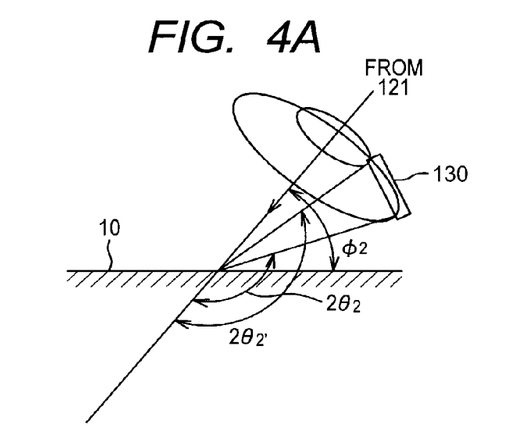

As illustrated in FIG. 4A, when the X-ray having a wavelength of λ, same as the wavelength of the X-ray from the first X-ray source 111, from the second X-ray source 121 is transmitted through the second slit device 124 to be shaped, and then, is incident on the region on the polycrystalline sample 10, which region is the same as the region where the X-ray from the first X-ray source 111 is irradiated, with an incident angle φ2, the diffracted X-ray is emanated according to the lattice indexing of the crystal of the sample 10. When the diffraction angle of the diffracted X-ray with respect to the advancing direction of the incident X-ray is defined as $2\theta_2$, the diffraction angle $2\theta_2$ is represented as an angle double the incident angle $\theta_2$ of the X-ray to the crystal plane of the sample 10. When the crystal plane of the sample 10 has random orientations, information relating to the respective crystal planes can be obtained, whereby the inside of the sample 10 can be observed without destroying the sample 10.

Figure 4B:
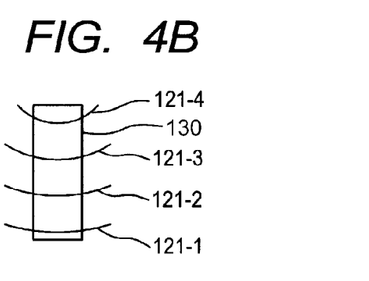
FIG. 4B is a front view of the X-ray detector.

FIG. 4B illustrates one example of a state in which the diffracted X-ray from the sample 10 is detected by the X-ray detector 130. Diffracted X-ray patterns according to the indexing of the crystal plane of the sample 10 are detected on the detection surface of the X-ray detector 130. Since the incident angle $\theta_2$ of the X-ray from the second X-ray source 121 to the sample 10 is different from the incident angle $\theta_1$ of the X-ray from the first X-ray source 111 to the sample 10, the concave patterns 121-1 to 121-4 of the diffracted X-ray on the detection surface of the X-ray detector 130 are detected such that the direction of the curvatures is opposite to the direction of the curvatures of the convex patterns 111-1 to 111-4 of the diffracted X-ray illustrated in FIG. 3B.

The diffraction angle $2\theta_2$ and $\theta_2$ of the diffracted X-ray and the crystal lattice length can be obtained from the positional relationship among the positional information of the diffracted X-ray patterns 121-1 to 121-4 on the X-ray detector 130 detected by the X ray detector 130, the position of the sample 10 where the X-ray is irradiated and the X-ray detector, and the information relating to the X-ray irradiation direction. In this case, the X-ray detector 130 can be replaced with a linear sensor.

Figure 5:
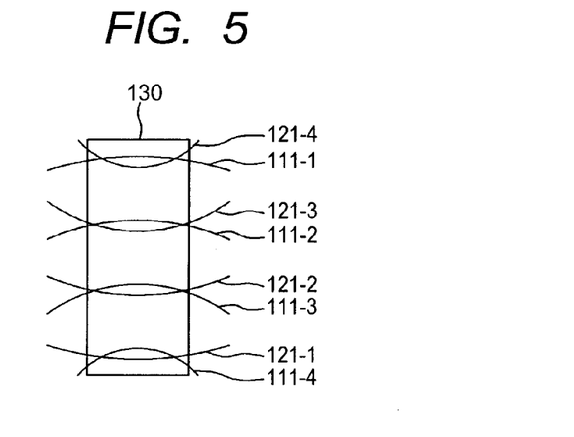
FIG. 5 is a front view of an X-ray detector illustrating a relationship among a Debye ring of a diffracted X-ray emanated when an X-ray is irradiated toward the sample from the first X-ray irradiating unit with the angle $\phi 1$, a Debye ring of a diffracted X-ray emanated when an X-ray is irradiated toward the sample from the second X-ray irradiating unit with the angle $\phi 2$, and the X-ray detector.

When the X-ray from the first X-ray source 111 and the X-ray from the second X-ray source 121 are simultaneously irradiated to the same region of the sample 10, the X-ray diffraction illustrated in FIG. 3A and the X-ray diffraction illustrated in FIG. 4A are simultaneously emanated from the sample 10, so that the diffraction patterns 111-1 to 111-4 convex in shapes and the diffraction patterns 121-1 to 121-4 concave in shapes as illustrated in FIG. 5 are detected by the X-ray detector 130. The X-ray diffraction pattern illustrated in FIG. 5 is a pattern formed by combining the convex diffraction patterns 111-1 to 111-4 generated by the irradiation of the X-ray from the first X-ray source 111 illustrated in FIG. 3B and the concave diffraction patterns 121-1 to 121-4 generated by the irradiation of the X-ray from the second X-ray source 121 illustrated in FIG. 4B.

In this case, the center direction of the curvature of each pattern is obtained from the output from the two-dimensional X-ray detector 130 detecting the X-ray diffraction patterns illustrated in FIG. 5, in order to separate the diffraction patterns 111-1 to 111-4 generated by the irradiation of the X-ray from the first X-ray source 111 and the diffraction patterns 121-1 to 121-4 generated by the irradiation of the X-ray from the second X-ray source 121.

The diffraction angles $2\theta_1$, $\theta_1$, $2\theta_2$ and $\theta_2$ of the diffracted X-ray and the crystal lattice length can be obtained from the positional relationship among the positional information on the X-ray detector 130 of each of separated patterns, the position of the sample 10 where the X-ray is irradiated, and the X-ray detector 130, and the X-ray irradiating direction.

The X-ray detector 130 is arranged as tilting with respect to the Debye ring formed by the diffraction patterns 111-1 to 111-4 generated by the irradiation of the X-ray from the first X-ray source 111 and the Debye ring formed by the diffraction patterns 121-1 to 121-4 generated by the irradiation of the X-ray from the second X-ray source 121, whereby the X-ray diffraction patterns detected by the two-dimensional X-ray detector 130 are detected as an ellipse that is deformed from a true circle. Accordingly, when the diffraction angles $2\theta_1$, $\theta_1$, $2\theta_2$ and $\theta_2$ of the diffracted X-ray are obtained, they may be calculated by using information of the major axis of the ellipse that is extracted from the elliptic X-ray diffraction pattern detected by the two-dimensional X-ray detector 130.

Figure 6:
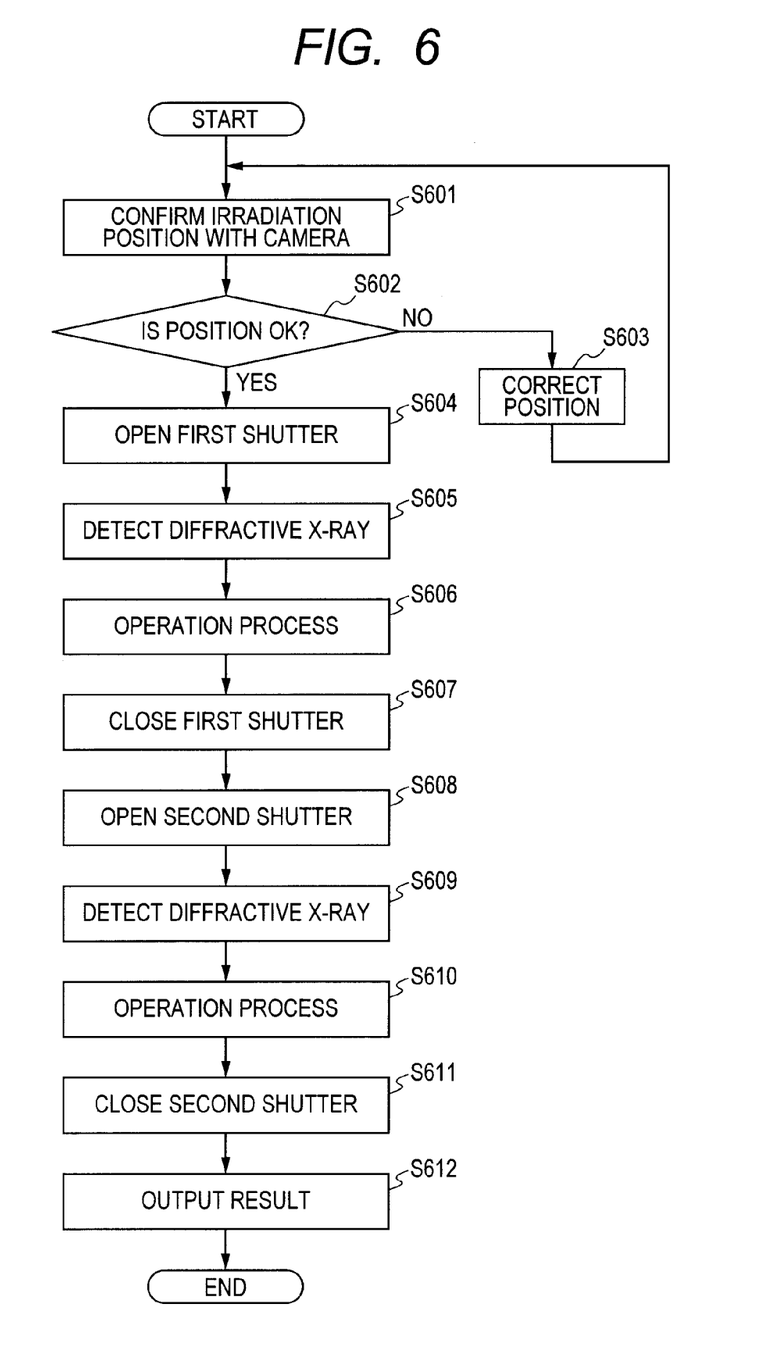
FIG. 6 is a flowchart for describing a procedure of detecting a diffracted X-ray by sequentially irradiating an X-ray toward the sample from the first X-ray irradiating unit and the second X-ray irradiating unit.

Next, the procedure of the operation of detecting the X-ray diffraction patterns by sequentially irradiating the X-ray onto the sample 10 from the first X-ray source 111 and the second X-ray source 121 with the use of the apparatus illustrated in FIG. 1 will be described with reference to FIG. 6.

Firstly, the X-ray diffraction apparatus 100 is set on the sample 10 to be measured, and with this state, the surface of the sample 10 below the transmissive window 103 is observed by the camera 140 through the window portion 104 so as to confirm whether or not the portion of the sample 10 that should be analyzed agrees with the position where the X-ray is irradiated (S601). When the position is determined to be shifted as a result of the observation (NO in S602), the position of the X-ray diffraction apparatus 100 or the sample 10 is adjusted (S603).

When it is determined that the position is not shifted as a result of the observation (YES in S602), the first actuator 113 is driven according to the instruction from the first shutter drive unit 152 of the processing control unit 150 so as to open the first shutter 112 arranged immediately before the first X-ray source 111 (S604), whereby the X-ray emitted from the first X-ray source 111 is transmitted through the first slit device 114 to be narrowed down and shaped, and then, irradiated to the sample 10 below the X-ray transmissive window 103. The diffracted X-ray, out of the diffracted X-rays emanated from the sample 10 to which the X-ray narrowed down by the first slit device 114 is irradiated, passing through the X-ray transmissive window 103 to be incident on the X-ray detector 130 is detected by the X-ray detector 130 (S605). The output from the X-ray detector 130 detecting the diffracted X-ray is inputted to the sensor input unit 156 of the processing control unit 150, amplified, subjected to an A/D conversion, and then, transmitted to the operation unit 157 where the diffraction angle $\theta_1$ is obtained through the operation process (S606).

Subsequently, the first actuator 113 is driven in accordance with the instruction from the first shutter drive unit 152 so as to close the first shutter 112 (S607), in order to shield the X-ray emitted from the first X-ray source 111 for preventing the X-ray from irradiating the sample 10. The second actuator 123 is driven in accordance with the instruction from the second shutter drive unit 154 so as to open the second shutter 122, which is arranged immediately before the second X-ray source 121 (S608), whereby the X-ray emitted from the second X-ray source 121 is transmitted through the second slit device 124 to be narrowed down and shaped, and then, irradiated to the region of the sample 10, same as the region where the X-ray emitted from the first X-ray source 111 is irradiated, through the X-ray transmissive window 103.

The diffracted X-ray, out of the diffracted X-rays emanated from the sample 10 to which the X-ray narrowed down by the second slit device 124 is irradiated, passing through the X-ray transmissive window 103 to be incident on the X-ray detector 130 is detected by the X-ray detector 130 (S609). The output from the X-ray detector 130 detecting the diffracted X-ray is inputted to the sensor input unit 156 of the processing control unit 150, amplified, subjected to an A/D conversion, and then, transmitted to the operation unit 157 where the diffraction angle $\theta_2$ is obtained through the operation process (S610).

Then, the second actuator 123 is driven in accordance with the instruction from the second shutter drive unit 154 to close the second shutter 122 (S611), in order to shield the X-ray emitted from the second X-ray source 121 for preventing the X-ray from irradiating to the sample 10.

Finally, information of the $\theta1$ obtained in S606 through the operation, $\theta2$ obtained in S610 through the operation are sent to the output unit 160 from the input/output unit 158, and the resultant is displayed onto the display screen 161 (S612).

According to the present embodiment, it takes some times because the X-ray is sequentially irradiated from the first X-ray source 111 and the second X-ray source 121. However, the X-ray diffraction patterns generated by the irradiation of the X-ray from the first X-ray source 111 and the X-ray diffraction patterns generated by the irradiation of the X-ray from the second X-ray source 121 can be detected as being surely separated from each other, whereby a high detection precision can be expected without changing the position of the X-ray detector.

Since the X-ray diffraction patterns can be detected in a continuous wide region by a linear or two-dimensional X-ray detector 130, a higher detection precision can be attained.

The X-ray detector 130 can be configured with a linear detector, and since the X-ray detector 130 is fixed, the apparatus does not have a movable mechanism other than the shutter. Therefore, the apparatus can be made compact and lightweight.

As a modification of the present embodiment, the on/off function of the drive source 151 for the first X-ray source 111 and the on/off function of the drive source 155 for the second X-ray source 121 can be used as a substitute operation of opening and closing the first shutter 112 and the second shutter 122. In this case, the shutter can be eliminated from the apparatus.

As another modification of the present embodiment, a drive high-voltage power source unit (not illustrated) of the first X-ray source 111 and the second X-ray source 121 can be shared, and it is electrically changed by a switch, whereby the weight of the apparatus can further be reduced.

The present embodiment does not need a goniometer conventionally used for adjusting a position of the X-ray detector, and does not have a movable mechanism other than the shutter. Therefore, the present embodiment can provide a compact and lightweight apparatus.

Second Embodiment

A second embodiment will be described below wherein the X-ray is simultaneously emitted from the first X-ray source 111 and the second X-ray source 121 so as to simultaneously irradiate the same region on the sample 10 with the use of the X-ray diffraction apparatus 100 having the configuration illustrated in FIG. 1. In this case, the pattern, as described in FIG. 5, is detected from the sample 10, wherein the pattern has the X-ray diffraction patterns by the irradiation of the X-ray from the first X-ray source 111 and the X-ray diffraction patterns by the irradiation of the X-ray from the second X-ray source 121, those of which are superimposed with each other.

Figure 7:
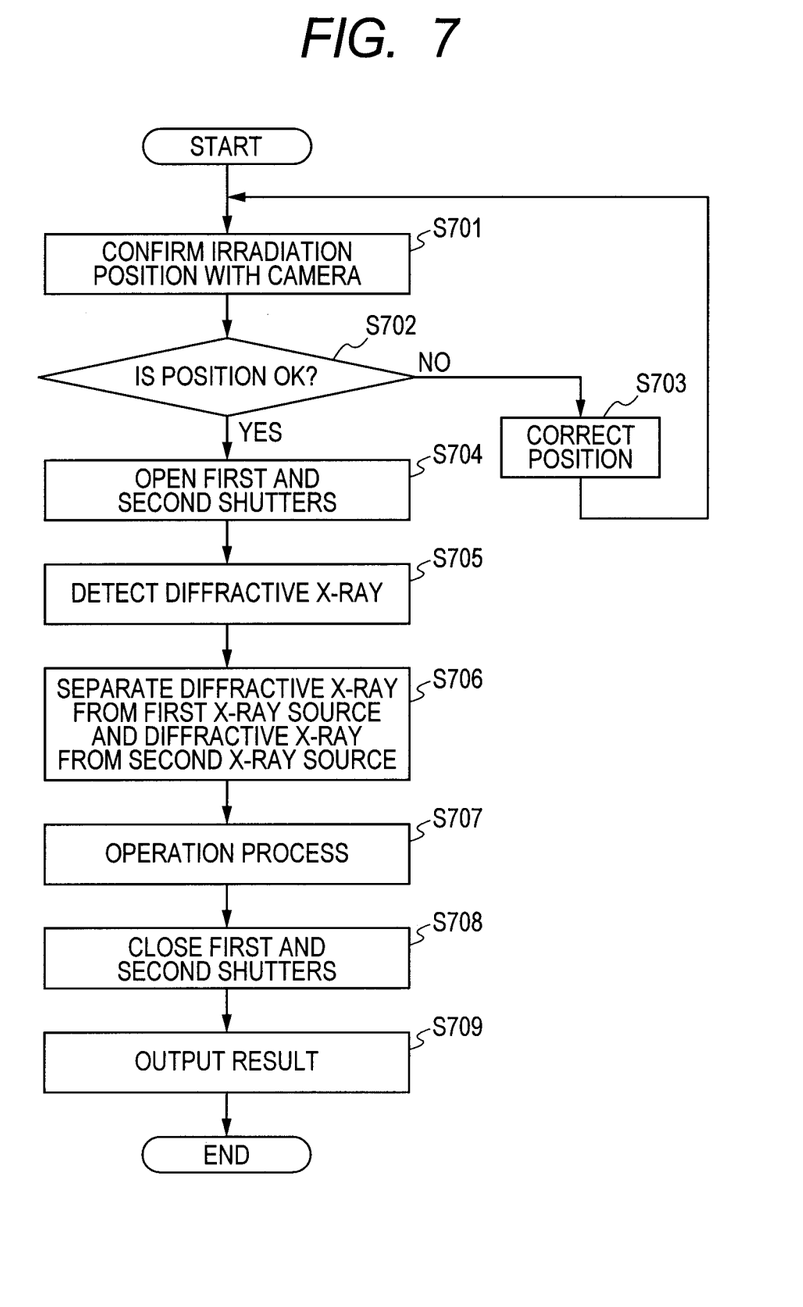
FIG. 7 is a flowchart for describing a procedure of detecting a diffracted X-ray by simultaneously irradiating an X-ray toward the sample from the first X-ray irradiating unit and the second X-ray irradiating unit.

The procedure of the detection in this case will be described with reference to FIG. 7.

Firstly, the X-ray diffraction apparatus 100 is set on the sample 10 to be measured, and with this state, the surface of the sample 10 below the transmissive window 103 is observed by the camera 140 through the window portion 104 so as to confirm whether or not the portion of the sample 10 that should be analyzed agrees with the position where the X-ray is irradiated (S701). When the position is determined to be shifted as a result of the observation (NO in S702), the position of the X-ray diffraction apparatus 100 or the sample 10 is adjusted (S703).

When it is determined that the position is not shifted as a result of the observation (YES in S702), the first actuator 113 is driven according to the instruction from the first shutter drive unit 152 of the processing control unit 150 so as to open the first shutter 112 arranged immediately before the first X-ray source 111, and simultaneously, the second actuator 123 is driven according to the instruction from the second shutter drive unit 154 so as to open the second shutter 122 arranged immediately before the second X-ray source 121 (S704), whereby the X-ray emitted from the first X-ray source 111 and shaped by the first slit device 114 and the X-ray emitted from the second X-ray source 121 and shaped by the second slit device 124 are transmitted through the X-ray transmissive window 103, and simultaneously irradiated onto the same region of the sample 10.

The diffracted X-ray, out of the diffracted X-rays emanated from the sample 10 to which the X-ray is irradiated, passing through the X-ray transmissive window 103 to be incident on the X-ray detector 130 is detected by the X-ray detector 130 (S705). The output from the X-ray detector 130 detecting the diffracted X-ray is inputted to the sensor input unit 156 of the processing control unit 150, amplified, subjected to the A/D conversion, and then, transmitted to the operation unit 157 where the X-ray diffraction patterns generated from the X-ray emitted from the first X-ray source 111 and the X-ray diffraction patterns generated from the X-ray emitted from the second X-ray source 121 are separated from each other (S706), and the diffraction angle $\theta_1$ of the X-ray diffraction patterns generated by the X-ray emitted from the first X-ray source 111 and the diffraction angle $\theta_2$ of the X-ray diffraction patterns generated by the X-ray emitted from the second X-ray source 121 are obtained through the operation process (S707).

Subsequently, the first actuator 113 is driven in accordance with the instruction from the first shutter drive unit 152 so as to close the first shutter 112, and simultaneously, the second actuator 123 is driven in accordance with the instruction from the second shutter drive unit 154 so as to close the second shutter 122 (S708), in order to shield the X-ray emitted from the first X-ray source 111 and the X-ray emitted from the second X-ray source 121.

Finally, the information of the $\theta_1$ and $\theta_2$ obtained in S707 through the operation is sent to the output unit 160 from the input/output unit 158, and the resultant is displayed onto the display screen 161 (S709).

According to the present embodiment, the X-rays are simultaneously irradiated from the first X-ray source 111 and the second X-ray source 121, whereby the time for the measurement can be shortened.

The X-ray diffraction patterns can be detected in a continuous wide region with the two-dimensional X-ray detector 130, whereby a higher detection precision can be attained.

Since the X-ray detector 130 is fixed, the apparatus does not have a movable mechanism other than the shutter. Therefore, the apparatus can be made compact and lightweight.

As a modification of the present embodiment, the on/off function of the drive source 151 for the first X-ray source 111 and the on/off function of the drive source 155 for the second X-ray source 121 can be used as a substitute operation of opening and closing the first shutter 112 and the second shutter 122. In this case, the shutter can be eliminated from the apparatus.

The present embodiment does not need a goniometer conventionally used for adjusting a position of the X-ray detector, and does not have a movable mechanism other than the shutter. Therefore, the present embodiment can provide a compact and lightweight apparatus.

Third Embodiment

A third embodiment according to the present invention will be described with reference to FIG. 8.

Figure 8:
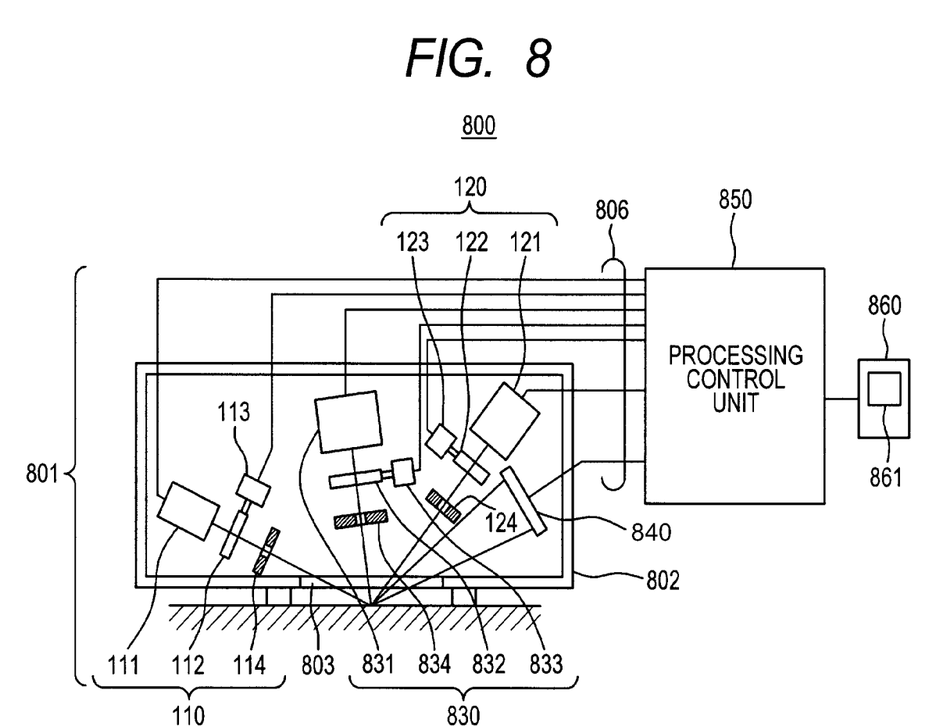
FIG. 8 is a block diagram illustrating an overall structure of an X-ray diffraction apparatus according to a third embodiment of the present invention.

The configuration illustrated in FIG. 8 is obtained by eliminating the monitor camera 140 of the X-ray diffraction apparatus 100 described in FIG. 1 and mounting a third X-ray irradiating unit 830. The elements which are the same with that of the first embodiment are put the same number with the FIG. 1. As in the first and second embodiments, an X-ray diffraction apparatus body 801 of the third embodiment includes the first X-ray irradiating unit 110, the second X-ray irradiating unit 120, the third X-ray irradiating unit 830, and an X-ray detector 840. These are arranged on the same plane in a container 802 illustrated in FIG. 8, wherein X-rays generated by the first to third X-ray irradiating units 110, 120, and 830 are transmitted through an X-ray transmissive window 803 to be irradiated onto the sample 10.

Figure 9:
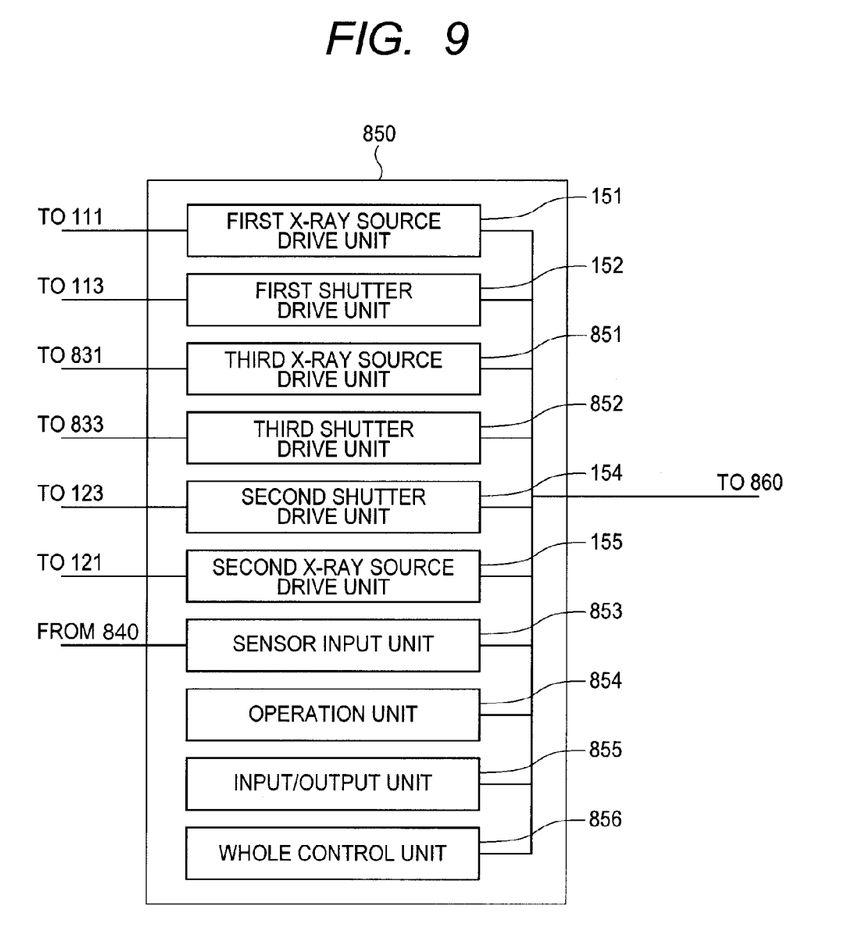
FIG. 9 is a block diagram illustrating a processing control unit of the X-ray diffraction apparatus according to the third embodiment of the present invention.

As illustrated in FIG. 9, a processing control unit 850 includes the first X-ray source drive unit 151 for driving the first X-ray source 111, the first shutter drive unit 152 for driving the first actuator 113, the second shutter drive unit 154 for driving the second actuator 123, the second X-ray source drive unit 155 for driving the second X-ray source 121, a third X-ray source drive unit 851 for driving the third X-ray source 831, a third shutter drive unit 852 for driving a third actuator 833, a sensor input unit 853 for receiving an output from the X-ray detector 840, an operation unit 854 for calculating an X-ray diffraction angle of the sample 10 by using the output from the X-ray detector 840 received by the sensor input unit 853, an input/output unit 855 that inputs information relating to the irradiation condition of the X-ray and the sample 10 and outputs information relating to the X-ray diffraction angle of the sample 10 calculated by the operation unit 854, and an entire control unit 856 that controls the entire apparatus. The respective units of the processing control unit 850 and the X-ray diffraction apparatus body 801 are separated, wherein they are connected with a cable 806.

The output unit 860 includes a display screen 861, and displays the information relating to the X-ray diffraction angle of the sample 10 outputted from the input/output unit 855 of the processing control unit 850 onto the display screen 861.

Like the first X-ray irradiating unit 110 and the second X-ray irradiating unit 120 described in FIG. 1, the third X-ray irradiating unit 830 includes the third X-ray source 831, the third shutter 832, the third actuator 833 for driving the third shutter 832 for opening and closing the third shutter 832, and a third slit device 834 for narrowing down the X-ray emitted from the third X-ray source 831.

The method of detecting the diffracted X-ray from the sample 10 with the use of the apparatus 800 having the above-mentioned configuration is the same as the method of detecting the X-ray diffraction patterns by sequentially irradiating the X-ray from each X-ray source as described in the first embodiment, and the method, as described in the second embodiment, in which the X-rays are simultaneously irradiated from the respective X-ray sources, and the X-ray diffraction patterns detected by the two-dimensional X-ray detector 130 are separated into each X-ray diffraction pattern for each X-ray source so as to obtain the diffraction angle.

The present embodiment describes the case in which three X-ray irradiating units are provided. However, the present invention is not limited thereto. The X-ray diffraction apparatus may be configured to include many X-ray irradiating units more than three.

In the present embodiment, plural X-ray irradiating units, each having a different X-ray irradiation angle, are provided to irradiate the X-ray onto the sample. Therefore, the diffracted X-ray in a wider range can be detected, which can enhance the precision in the X-ray diffraction.

Since the X-ray diffraction patterns can be detected in a continuous wide region by the two-dimensional X-ray detector 840, a higher detection precision can be attained.

When the present embodiment takes a method same as the method described in the first embodiment in which the X-ray is sequentially irradiated from each X-ray source so as to detect the X-ray diffraction patterns, a drive high-voltage power source unit (not illustrated) of the first X-ray source 111, the second X-ray source 121, and the third X-ray source 831 can be shared, and it is electrically changed by a switch, whereby the weight of the apparatus can further be reduced, as a modification of the present embodiment.

When the present embodiment takes a method same as the method described in the second embodiment in which the X-rays are simultaneously irradiated from the respective X-ray sources, the on/off function of the drive source 151 for the first X-ray source 111, the on/off function of the drive source 155 for the second X-ray source 121, and the on/off function of the drive source 851 for the third X-ray source 831 can be used as a substitute operation of opening and closing the first shutter 121, the second shutter 122 and the third shutter 832. In this case, the shutters can be eliminated from the apparatus, as another modification of the present embodiment.

The slit device is one of X-ray forming units, and it can be replaced with an X-ray optical device such as a capillary tube, zone plate, or a collimator. Specifically, the first slit device 114 is a first X-ray forming unit, the second slit device 124 is a second X-ray forming unit, and the third slit device 834 is a third X-ray forming unit.

The present embodiment does not need a goniometer conventionally used for adjusting a position of the X-ray detector, and does not have a movable mechanism other than the shutter. Therefore, the present embodiment can provide a compact and lightweight apparatus.

The invention may be embodied in other specific forms without departing from the spirit or essential characteristics thereof. The present embodiment is therefore to be considered in all respects as illustrative and not restrictive, the scope of the invention being indicated by the appended claims, rather than by the foregoing description, and all changes which come within the meaning and range of equivalency of the claims are therefore intended to be embraced therein.

INDUSTRIAL APPLICABILITY

The present invention is applicable to a portable X-ray diffraction apparatus using a method for X-ray diffraction for analyzing a material by irradiating a characteristic X-ray, generated from an X-ray tube, onto a sample.

REFERENCE SIGNS LIST

10 Sample
100 X-ray diffraction apparatus
101 X-ray diffraction apparatus body
102 Container
103 X-ray transmissive window
104 Monitor glass window
105 X-ray shied ring
110 First X-ray irradiating unit
111 First X-ray source
112 First shutter
114 First slit device
120 Second X-ray irradiating unit
121 Second X-ray source
122 Second shutter
124 Second slit device
130 X-ray detector
140 Monitor camera
150 Processing control unit
160 Output unit

The invention claimed is:

1. An X-ray diffraction apparatus comprising:
a plurality of X-ray irradiating units that irradiate a plurality of shaped X-rays from different directions onto a same region on a surface of a sample;
an X-ray detecting unit that detects, with a sensor which is inclined in a direction towards the plurality of the shaped X-rays which are incident on the sample, a plurality of diffracted X-rays that are reflected from the same region on the surface of the sample by the irradiation of the X-rays from the plurality of X-ray irradiating units; and
an X-ray diffraction signal processing unit that processes signals acquired by detecting the plurality of diffracted X-rays that are reflected from the same region on the surface of the sample by the X-ray detecting unit,
wherein a plurality of different diffraction X-ray patterns are respectively caused by the plurality of the diffracted X-rays and detected by the sensor of the X-ray detecting unit,
wherein each of the X-ray patterns has a curved shape, and
wherein the X-ray diffraction signal processing unit extracts axis information of an elliptical shape including a center direction of curvature from each of the curved X-ray patterns and calculates a crystal lattice length of the sample therefrom.

2. An X-ray diffraction apparatus according to claim 1, wherein each of the plurality of X-ray irradiating units irradiates the shaped X-rays which have a same wavelength onto the same region on the surface of the sample.

3. An X-ray diffraction apparatus according to claim 1, wherein the sensor is a single two-dimensional X-ray detector.

4. An X-ray diffraction apparatus according to claim 3, wherein the X-ray diffraction signal processing unit performs a process of separating signals, corresponding to the plurality of diffracted X-rays reflected from the same region on the surface of the sample, from simultaneous irradiation of the shaped X-rays which have a same wavelength from the plural X-ray irradiating units.

5. An X-ray diffraction apparatus according to claim 1, wherein the plurality of X-ray irradiating units include:

a first X-ray irradiating unit that irradiates a plurality of first shaped X-rays onto the surface of the sample from a first direction; and a second X-ray irradiating unit that irradiates, from a second direction, a plurality of second shaped X-rays on the same region on the surface of the sample where the first X-ray irradiating unit irradiates the first shaped X-rays, wherein the first shaped X-rays and the second shaped X-rays have a same wavelength, wherein the X-ray detecting unit detects a plurality of first diffracted X-rays that are reflected from the same region on the surface of the sample where the first shaped X-rays are irradiated from the first X-ray irradiating unit and a plurality of second diffracted X-rays that are reflected from the same region on the surface of the sample where the second shaped X-rays are irradiated from the second X-ray irradiating unit, wherein the X-ray diffraction signal processing unit processes signals obtained by detecting the first diffracted X-rays and the second diffracted X-rays that are reflected from the same region on the surface of the sample with the sensor of the X-ray detecting unit, and wherein a one of the diffraction X-ray patterns which is caused by the first diffracted X-rays has a curved shape which is opposite to a curved shape of another one of the diffraction X-ray patterns which is caused by the second diffracted X-rays.

6. An X-ray diffraction apparatus according to claim 5, further comprising:

a container unit that contains the first and second X-ray irradiating units and the X-ray detecting unit;

a control unit that controls the first and second X-ray irradiating units and the X-ray detecting unit contained in the container unit; and a cable that connects the container unit and the control unit, wherein the container unit and the control unit are separated from each other, and the container unit and the control unit are connected with the cable, and signals are received and transmitted between the plurality of X-ray irradiating units and the X-ray detecting unit, and the control unit via the cable.

7. An X-ray diffraction apparatus according to claim 1, further comprising:

an imaging unit that images the same region of the surface of the sample where the X-rays are irradiated from the plurality of X-ray irradiating units; and a monitor unit that displays an image of the same region on the surface of the sample where the X-rays are irradiated from the plurality of X-ray irradiating units which is acquired by the imaging unit.

8. An X-ray diffraction apparatus according to claim 1, wherein the plurality of X-ray irradiating units and the X-ray detecting unit are located on a same side of the sample, and the plurality of X-ray irradiating units irradiate the shaped X-rays from different directions and different angles onto the same region on the surface of the sample.

9. An X-ray diffraction apparatus according to claim 1, wherein the X-ray diffraction signal processing unit processes signals acquired by detecting the plurality of diffracted X-rays that are reflected from the same region on the surface of the sample by the X-ray detecting unit to separate the diffraction X-ray patterns respectively caused by ones of the plurality of the diffracted X-rays.

10. A method for X-ray diffraction comprising:

irradiating a plurality of shaped X-rays from a plurality of X-ray irradiating units onto a same region on a surface of a sample from different directions;

detecting, by an X-ray detecting unit with a sensor which is inclined in a direction towards the plurality of shaped X-rays which are incident on the sample, a plurality of diffracted X-rays that are reflected from the same region on the surface of the sample by the irradiation of the X-rays from the plurality of X-ray irradiating units; and processing, by an X-ray diffraction signal processing unit, signals acquired from the detecting of the plurality of diffracted X-rays that are reflected from the same region on the surface of the sample with the X-ray detecting unit;

wherein a plurality of different diffraction X-ray patterns are respectively caused by the plurality of the diffracted X-rays and detected by the sensor of the X-ray detecting unit, wherein each of the X-ray patterns has a curved shape, and wherein the processing by the X-ray diffraction signal processing unit includes extracting axis information of an elliptical shape including a center direction of curvature from each of the curved X-ray patterns and calculating a crystal lattice length of the sample therefrom.

11. A method for X-ray diffraction according to claim 10, wherein the shaped X-rays have a same wavelength and are irradiated from the plurality of X-ray irradiating units onto the same region on the surface of the sample.

12. A method for X-ray diffraction according to claim 10, sensor is a single two-dimensional X-ray detector.

13. A method for X-ray diffraction according to claim 12, wherein the processing by the X-ray diffraction signal processing unit further includes separating the signals, corresponding to the plurality of diffracted X-rays reflected from the same region on the surface of the sample, from simultaneous irradiation of the shaped X-rays which have a same wavelength from the plurality of X-ray irradiating units.

14. A method for X-ray diffraction according to claim 10, wherein the shaped X-rays are irradiated from the plurality of X-ray irradiating units onto the same surface of the sample from different directions in such a manner that a plurality of first shaped X-rays are irradiated onto the surface of the sample by a first X-ray irradiating unit from a first direction, and a plurality of second shaped X-rays, having the same wavelength as the first shaped X-rays irradiated from the first X-ray irradiating unit, are irradiated on the same region on the surface of the sample where the first shaped X-rays are irradiated, from a second X-ray irradiating unit from a second direction, wherein the detecting of the diffracted X-rays includes detecting a plurality of first diffracted X-rays that are reflected from the same region on the surface of the sample where the first shaped X-rays are irradiated from the first X-ray irradiating unit and a plurality of second diffracted X-rays that are reflected from the same region on the surface of the sample where the second X-rays are irradiated from the second X-ray irradiating unit, and wherein the processing includes processing signals obtained by detecting the first diffracted X-rays and the second diffracted X-rays that are reflected from the same region on the surface of the sample, wherein one of the diffraction X-ray patterns caused by the first diffracted X-rays has a curved shape which is opposite to a curved shape of another one of the diffraction X-ray patterns caused by the second diffracted X-rays.

15. A method for X-ray diffraction according to claim 10, further comprising:

processing the signals obtained by detecting the plurality of diffracted X-rays that are reflected from the same region on the surface of the sample through the irradiation of the X-rays from the plurality of X-ray irradiating units at a location separated from the plurality of X-ray irradiating units and connected via a cable.

16. A method for X-ray diffraction according to claim 10, further comprising:
   imaging a region of the surface of the sample where the X-rays are irradiated from the plurality of X-ray irradiating units; and
   displaying an image of the region on the surface of the sample where the X-rays are irradiated from the plurality of X-ray irradiating units acquired by the imaging on a monitor screen at a location separated from the plurality of X-ray irradiating units.

17. A method for X-ray diffraction according to claim 10, wherein the plurality of X-ray irradiating units and the X-ray detecting unit are located on a same side of the sample, and the plurality of X-ray irradiating units irradiate the shaped X-rays from different directions and different angles onto the same region on the surface of the sample.

18. A method for X-ray diffraction according to claim 10, wherein the processing of the signals acquired from the detecting of the plurality of diffracted X-rays that are reflected from the same region on the surface of the sample with the X-ray detecting unit includes separating the diffraction X-ray patterns respectively caused by ones of the plurality of the diffracted X-rays.

\* \* \* \* \*